United States Patent [19]

Berthold et al.

[11] 4,332,941
[45] Jun. 1, 1982

[54] CYCLOHEXANONES AND CYCLOHEXENONES

[75] Inventors: Rüdiger Berthold, Bad Soden am Taunus; Werner H. Müller, Eppstein, both of Fed. Rep. of Germany

[73] Assignee: Hoechst Aktiengesellschaft, Frankfurt am Main, Fed. Rep. of Germany

[21] Appl. No.: 195,840

[22] Filed: Oct. 10, 1980

[30] Foreign Application Priority Data

Oct. 13, 1979 [DE] Fed. Rep. of Germany ....... 2941625

[51] Int. Cl.³ .............................................. C07D 401/12
[52] U.S. Cl. .................................... 546/191; 546/208; 546/238; 546/239; 544/87; 544/130; 544/141; 544/162; 260/456 R; 560/38; 560/126; 560/127; 568/338; 564/86; 564/87; 564/88; 564/169; 564/166; 564/162; 548/523; 548/573
[58] Field of Search ......................... 560/38, 126, 127; 546/208, 191, 238, 239; 260/326.37, 326.43; 544/87, 130, 141, 162

[56] References Cited

U.S. PATENT DOCUMENTS 2,581,840  1/1952  Drake et al. ........................ 560/126
2,798,793  7/1957  Moore ................................ 560/126
4,220,799  9/1980  Berthold et al. .................... 560/126

Primary Examiner—Robert T. Bond
Attorney, Agent, or Firm—Curtis, Morris & Safford

[57] ABSTRACT

Cyclohexanones and -hexenones

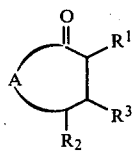 (1)

wherein A is

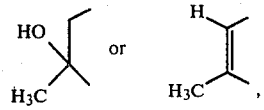

(1a)            (1b)

$R^1$ is hydrogen or $$-CO-O-C_nH_{2n+1-m}(-NR^4R^5) \quad (1c)$$

$R^2$ is a group 1c, $R^3$ is $C_1$- to $C_{10}$-alkyl, phenyl or phenyl substituted by lower alkyl, lower alkoxy, trifluoromethyl, nitro, cyano, chloro, carbamoyl, lower-alkyl-carbamoyl, sulfamoyl or lower-alkyl-sulfamoyl, $R^4$ and $R^5$ are lower alkyl or $-NR^4R^5$ is pyrrolidinyl, piperidyl or morpholyl, m is 1 or 2 and n is 2 to 6, are obtained by reacting 2 mols of an ester $$CH_3-CO-CH_2-CO-O-C_nH_{2n+1-m}(-NR^4R^5)_m \quad (2)$$

with an aldehyde $R^3$—CHO (3). The compounds (1) easily saponify and decarboxylate without an added catalyst to form a cyclohexenones

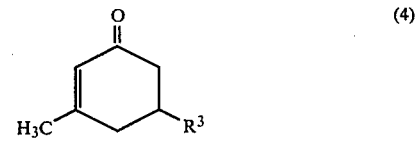 (4)

while setting free the alcohol $$HO-C_nH_{2n+1-m}(-NR^4R^5)_m \quad (5)$$

which reacts without a catalyst with diketene to form the ester (2). Thus, in effect, 2 mols of diketene and 1 mol of aldehyde (3) form 1 mol of (4) and 2 mols of carbon dioxide as sole by-product. (4) can be transformed via the oxime to the correspondingly 5-substituted 3-methylaniline.

10 Claims, No Drawings

CYCLOHEXANONES AND CYCLOHEXENONES

It is known from German Offenlegungsschrift No. 2,654,850 (U.S. Pat. No. 4,220,799) to prepare substituted cyclohexanones and cyclohexenones from acetoacetic esters and aldehydes, these condensation reactions being carried out in the presence of catalytic amounts of aliphatic tertiary amines. The amines added act also as catalysts for the separation of water from the cyclohexanolones obtained in the first reaction step to give cyclohexenones, as well as for the saponification of the carboxylic acid ester group in α-position to the keto group and the resulting carboxy group easily decarboxylizes. For the saponification of the second carboxylic acid ester group, however, it is necessary to add an acid as catalyst.

Subject of the invention are compounds of the formula (1)

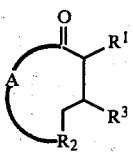
(1)

in which

A is a group of the formula (1a) or (1b)

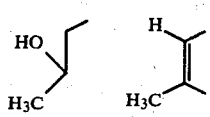
(1b)

which completes formula (1) to represent a carbocyclic six-membered ring, $R^1$ is hydrogen or a group of the formula (1c)

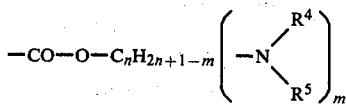
(1c)

$R^2$ is a group of the formula (1c), $R^3$ is hydrogen, alkyl with from 1 to 10 carbon atoms, unsubstituted phenyl or phenyl substituted by lower alkyl, lower alkoxy, trifluoromethyl, nitro, cyano, chlorine or carbamoyl or sulfamoyl radicals, which latter groups can be substituted by lower alkyl, $R^4$ and $R^5$, which are identical or different are lower alkyl or form a pyrrolidine, piperidine or morpholine ring together with the nitrogen atom, m is 1 or 2 and n is from 2 to 6.

"Lower" alkyl or alkoxy here and in the following means radicals with up to 4, preferably 1 or 2, carbon atoms.

Subject of the invention is, furthermore, a process for the manufacture of the compounds of the formula (1) which comprises reacting 2 mols of a compound of the formula (2)

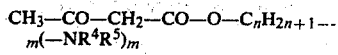
(2)

with 1 mol of an aldehyde of the formula (3)

(3)

Subject of the invention is, furthermore, the use of compounds of the formula (1) for preparing compounds of the formula (4)

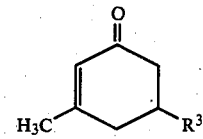
(4)

by saponification and decarboxylation. The compounds of the formula (4) are known and are used, for example, for preparing the correspondingly substituted anilines via the intermediate stage of the cyclohexanonoximes (German Offenlegungsschriften Nos. 2,654,851 (U.S. Pat. No. 4,128,579) and 2,654,852).

In comparison with the compounds known from German Offenlegungsschrift No. 2,654,850, the compounds according to the invention have the advantage that the saponification and decarboxylation of the second ester group, too, can be performed without addition of a catalyst. Thus, it is not necessary to separate a catalyst which facilitates the isolation of the product and, in particular, of the split off alcohol of the formula (5)

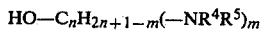
(5)

Thus, this alcohol can easily be recovered and be converted into the starting compound of the formula (2), for example by diketene. Even for this reaction, contrary to the unsubstituted alkanols, no catalyst is necessary. Thus, the invention permits the manufacture of compounds of the formula (4) from 2 mols of diketene and 1 mol of the aldehyde of the formula (4), which process requires no catalyst and carbon dioxide is the only by-product.

Another advantage in comparison with the process known from German Offenlegungsschrift No. 2,654,850 is that the process according to the invention can easily be performed in such a way that the compounds of the formula (1) remain in liquid state and thus can easily be withdrawn from the reaction vessel. Since the products are free from catalysts and can be converted into the compounds of the formula (4) without further additives, expensive purification operations can be dispensed with.

The starting compounds of the formula (2) are known and can easily be obtained from diketenes and the corresponding alcohol, as mentioned above. Since the type of the alcohol (5) does not have any importance for the use of the new compounds according to the invention, there are suitably chosen easily accessible and easily separable alcohols (5). Therefore, compounds with m being 1 and n being 2 or 3 and $R^4$ and $R^5$ being identical and meaning methyl or ethyl are preferably used. The use of other compounds of the formula (2) is possible, but without advantage for the use according to the invention.

Preferred aldehydes of the formula (3) are alkanals with up to 5 carbon atoms, especially with from 2 to 4 carbon atoms. Among the aromatic aldehydes unsubstituted benzaldehyde or benzaldehydes substituted by methyl, methoxy and chlorine are preferably used.

The reaction of the compounds (2) with the aldehyde (3) can be performed at a temperature between about −40° and 120° C. A temperature between about 0° and 80° C., especially between 20° and 70° C., is preferred. It is possible to carry out the process according to the invention in the presence of an inert solvent or diluent. It is also possible to use an excess of ester (2).

The operational conditions depend, of course, on the reactivity of the starting materials and on the type of the desired product. In general, the primary products, that is the cyclohexanolones of the formula (1a), wherein $R^1$ means the group (1c) are not isolated but subjected immediately to the water separation step yielding the compounds of the formula (1b). Since the carboxylic ester group adjacent to the keto group can likewise be split off easily, there is obtained in general the product of the formula (1), wherein $R^1$ is hydrogen.

Isolation of the compounds of the formula (1) is not necessary for their use according to the invention. Thus, condensation and saponification/decarboxylation can be performed in a one-pot reaction.

The water split off during the condensation is generally sufficient for the saponification of the ester group adjacent to the keto group. For the quantitative saponification of the second ester group water is added to the batch and the reaction mixture is heated. Heating can be performed in the open vessel or—for shortening the reaction time—under pressure.

The following examples illustrate the invention. Percentages are by weight, unless otherwise stated.

EXAMPLE 1

22.5 g of acetaldehyde (0.51 mol) are so slowly added with stirring to 173 g of acetoacetic acid 2-dimethylamino ethyl ester (1.0 mol, boiling point 106°–107° C. at 2.66 mbar), that the temperature does not exceed 50° C. After the addition of only about 7 g of acetaldehyde within 3 minutes the temperature already increases from 22° to 42° C. When all acetaldehyde has been added, stirring is continued for 20 minutes without cooling, the product is heated to 80° C. and stirring is continued for 5 hours under reflux. 173 g of product are obtained, which corresponds to a loss of about 22 g=0.5 mol of carbon dioxide.

The product is first distilled in the water jet vacuum at the descending condenser at a heating bath temperature of 100° C., then in the oil pump vacuum (2.7 mbar) likewise at 100° C. bath temperature, the low boiling fractions (water, dimethylaminoethanol and some 3,5-dimethylcyclohex-2-en-1-one) passing over thereby. The distillation residue (106 g) consists of 98% of 3,5-dimethylcyclohex-2-en-1-one-4-carboxylic acid 2'-dimethylamino ethyl ester and 2% of high boiling products. This corresponds to 104 g of (crude) ester, or 87% of the theory.

This crude ester can be directly further processed. It can be distilled (boiling point at 2.66 mbar 162° C.), but with little decomposition. The yellow distillation product has a degree of purity of about 90%. The rest consists of lower boiling products (dimethylaminoethanol, 3,5-dimethylcyclohex-2-en-1-one), which can be removed at a bath temperature of about 100° C. and a pressure of about 2.7 mbar without a column. The distillation residue represents 10% of the feed quantity.

EXAMPLE 2

36 g of butyraldehyde (0.5 mol) are added all at once while stirring to 173 g of freshly distilled acetoacetic acid 2-dimethylamino-ethyl ester (1.0 mol). During this process the temperature rises within 10 minutes to 51° C. and during further stirring it rises within 30 minutes to 61° C. 5 ml of water are added and stirring is continued for 1 hour at 80° C. under reflux. Subsequently the low boiling portions are withdrawn at a bath temperature of 120° C. and a vacuum of 2.7 mbar. The residue consists of 120 g of crude 3-methyl-5-propyl-cyclohex-2-en-1-one-4-carboxylic acid 2'-dimethylaminoethyl ester, of 91% purity, corresponding to 110 g of a product of 100% purity or to 82.3% of the theoretical yield. As distillation product there are obtained 65 g of a colorless liquid consisting of 81% of dimethylaminoethanol (0.59 mol).

The crude ester can be distilled only in small portions (about 30 to 50 g). The boiling point at 1.5 mbar is at 170°–172° C., the purity is 96%.

About 10% of the feed quantity remain as residue. Greater amounts may be distilled in a thin-layer distillation apparatus.

EXAMPLE 3

53 g (0.5 mol) of benzaldehyde are added all at once to 183 g (1.0 mol) of freshly distilled acetoacetic acid 2-dimethylaminoethyl ester. Within 10 minutes the temperature rises to 40° C. and then gradually drops. The reaction mixture is stirred overnight and thereby forms a crystal slurry. Suction-filtration gives 50 g of 3-phenyl-5-methylcyclohexan-5-ol-1-one-2,4-di-(carboxylic acid 2'-dimethylaminoethyl ester) in the form of fatty crystals having a melting point of from 123°–124° C., which corresponds to a yield of 26% of the theory, and 170 g of an oil.

The oil is heated for 6 hours to 80° C. and subsequently the low boiling fractions are separated as described in Examples 1 and 2. There are obtained 98 g of 3-methyl-5-phenyl-cyclohex-2-en-1-one-4-carboxylic acid 2'-dimethylaminoethyl ester of 90% purity, which corresponds to 88 g of a product of 100% purity or to a yield of the theory of 58.7%. This crude ester cannot be distilled in an oil pump vacuum.

A second crystalline fraction is obtained, when keeping the above-specified oil in the refrigerator for some days.

EXAMPLE 4

12 g of acetaldehyde (0.25 mol) are added while stirring all at once to 95 g of freshly distilled acetoacetic acid 1-dimethylamino-2-propyl ester (boiling point at 0.95 mbar 74°–75° C.) of 98% purity (0.5 mol). The temperature rises from 19° to 50° C. within 5 minutes. Stirring is continued for half an hour, whereupon the product is heated for 5 hours to 80° C. The low boiling fractions are separated at a bath temperature of 110° C. under a pressure of at most 2.7 mbar. This gives 61.3 g of crude 3,5-dimethylcyclohex-2-en-1-one-4-carboxylic acid 1'-dimethylamino-2'-propyl ester of 98% purity, which corresponds to 60 g of a product of 100% purity or to a theoretical yield of 95%. The ester can be easily distilled (boiling point at 2.7 mbar 156°–157° C.) whereby there are obtained 82% of the theory of a 100% purity product.

EXAMPLE 5

To 346 g of freshly distilled acetoacetic acid 2-dimethylaminoethyl ester (2.0 mols) there are added slowly 44 g of acetaldehyde (1.0 mol). The mixture is stirred for 1 hour at room temperature and for 5 hours at 80° C.

Dimethylaminoethanol and some water are subsequently distilled at a bath temperature of 100° C. 115 g of distilled product are obtained, which consists of 15% (17.3 g) of water and of 85% (97.8 g) of dimethylaminoethanol. The residue consists of 230 g of a mixture of 2.5% of 3,5-dimethylcyclohex-2-en-1-one, 1.5% of dimethylaminoethanol and of 96% of 3,5-dimethylcyclohex-2-en-1-one-4-carboxylic acid 2'-dimethylaminoethyl ester. This residue is heated together with 230 g of water or of distillate from the preceding operation in the autoclave for 5 hours to 140° C. Distillation on a column yields at a boiling point of up to 102° C. 285 g of a fraction (this fraction includes 10 g of 3,5-dimethylcyclohex-2-en-1-one, which has distilled with the water vapor and is separated). This aqueous ketone-containing phase is reused in the following saponification step. The further fractions obtained are: 52 g of dimethylaminoethanol in a boiling range of from 102°–135° C. and 89 g of 3,5-dimethylcyclohex-2-en-1-one in a boiling range of from 93°–110° C. at 24 mbar. This corresponds to an overall yield of 99 g of 3,5-dimethylcyclohex-2-en-1-one (79.8% of the theory).

EXAMPLE 6

To 72.5 g of acetoacetic acid 1,3-di-(dimethylamino)-2-propyl ester of 92% purity there are added 6.5 g of acetaldehyde. The temperature rises from 26° to 53° C. The product is stirred subsequently for 1 hour without heating and for 5 hours at 80° C. The subsequent distillation of the reaction mixture in vacuo gives as a forerun 20 g of a fraction which distills in a boiling range of from 49° to 172° C. at 1.1 to 2 mbar and consists of water and 1,3-di-(dimethylamino)-2-propanol and as the main fraction 3,5-dimethylcyclohex-2-en-1-one-4-carboxylic acid-1',3'-di-(dimethylamino)-2'-propyl ester having a boiling point of from 177° to 178° C. at 2.66 mbar. After distillation during which a little ester decomposes, 29 g of pure product are obtained, which corresponds to a yield of 67% of the theory.

EXAMPLE 7

3,5-Dimethylcyclohex-2-1-one-4-carboxylic acid-1'-diethylamino-2'-propyl ester having a boiling point of from 168° to 170° C. at 1.6 mbar are prepared in the manner described in Example 6 from acetoacetic acid-1-diethylamino-2-propyl ester and acetaldehyde. The yield amounts to 72% of the theory.

EXAMPLE 8

3,5-Dimethylcyclohex-2-en-1-one-4-carboxylic acid-1'-piperidyl-2'-propyl ester having a boiling point of from 187°–189° C. at 2.66 mbar (decomp.) are prepared in the manner described in Example 6 from acetoacetic acid-1-piperidyl-2-propyl ester and acetaldehyde. The yield is 50% of the theory (according to gas chromatographic analysis the crude yield prior to distillation amounts to 80–90% of the theory).

We claim:
1. A compound of the formula

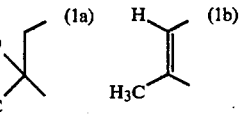

in which
A is a group of the formula (1a) or (1b) which complete formula (1) to a carbocyclic 6-membered ring,

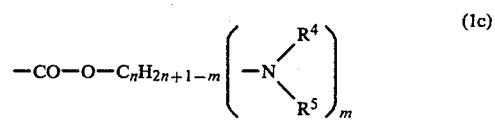

$R^1$ is hydrogen or a group of the formula (1c)

$$-CO-O-C_nH_{2n+1-m}\left(-N\diagup_{R^5}^{R^4}\right)_m \quad (1c)$$

$R^2$ is a group of the formula (1c),
$R^3$ is hydrogen, alkyl of 1 to 10 carbon atoms, phenyl, phenyl substituted by 1 to 3 equal or different substituents selected from the group consisting of lower alkyl, lower alkoxy, trifluoromethyl, nitro, cyano, chloro, carbamoyl, sulfamoyl or mono- or di-(lower alkyl)-carbamoyl or -sulfamoyl,
$R^4$ and $R^5$, which are the same or different, are lower alkyl or $-NR^4R^5$ is pyrrolidinyl, piperidyl or morpholyl,
m is 1 or 2 and
n is 2 to 6.
2. A compound as claimed in claim 1, wherein A is a group of the formula (1a) and $R^1$ is a group of the formula (1c).
3. A compound as claimed in claim 1, wherein A is a group of the formula (1b) and $R^1$ is hydrogen.
4. A compound as claimed in claim 1, wherein $R^3$ is hydrogen, alkyl of 1 to 4 carbon atoms, phenyl or phenyl substituted by methyl, methoxy and/or chlorine.
5. A compound as claimed in claim 1, wherein $R^4$ and $R^5$ are methyl or ethyl or $-NR^4R^5$ is piperidyl, m is 1 and n is 2 or 3.
6. A compound as claimed in claim 3, wherein m is 1, n is 2 or 3, $R^3$ is alkyl of 1 to 3 carbon atoms or phenyl and $R^4$ and $R^5$ are methyl or ethyl.
7. The compound as claimed in claim 6, wherein $R^3$ is methyl and $R^2$ is 2-dimethylamino-ethyl.
8. The compound as claimed in claim 6, wherein $R^3$ is phenyl and $R^2$ is 2-dimethylamino-ethyl.
9. The compound as claimed in claim 6, wherein $R^3$ is methyl and $R^2$ is 1-dimethylamino-2-propyl.
10. The compound as claimed in claim 6, wherein $R^3$ is methyl and $R^2$ is 1-diethylamino-2-propyl.

* * * * *